United States Patent [19]
Killick et al.

[11] Patent Number: 5,942,542
[45] Date of Patent: Aug. 24, 1999

[54] INSECTICIDE ADJUVANTS

[75] Inventors: Robert William Killick, Mt. Waverly; Andrew Robert Killick, Richmond; Peter Ronald Wrigley, Blackburn; Peter William Jones, Menzies Creek, all of Australia

[73] Assignee: Victorian Chemical International Pty Ltd., Richmond, Australia

[21] Appl. No.: 08/997,889

[22] Filed: Dec. 24, 1997

[30] Foreign Application Priority Data

Sep. 29, 1996 [AU] Australia ................................ PN5698

[51] Int. Cl.$^6$ ............................ A01N 37/34; A01N 53/00
[52] U.S. Cl. .......................... 514/521; 514/531; 514/975
[58] Field of Search .................................. 504/116, 117; 560/205, 190; 514/531, 975, 65, 521; 424/405

[56] References Cited

U.S. PATENT DOCUMENTS

| | | | |
|---|---|---|---|
| 4,083,954 | 4/1978 | Tsuchiya et al. | 424/47 |
| 4,664,847 | 5/1987 | Williams | 252/522 |
| 4,698,222 | 10/1987 | Grinda et al. | 421/19 |
| 5,288,483 | 2/1994 | Cardin et al. | 424/70 |
| 5,462,912 | 10/1995 | Hoiki et al. | 504/116 |
| 5,525,576 | 6/1996 | Medina-Vega et al. | 504/116 |
| 5,631,205 | 5/1997 | Killick et al. | |

FOREIGN PATENT DOCUMENTS

| | | |
|---|---|---|
| 0394847 | 10/1990 | European Pat. Off. |
| 06305904 | 11/1994 | Japan . |
| 2058569 | 4/1981 | United Kingdom . |
| 94/24858 | 11/1994 | WIPO . |

OTHER PUBLICATIONS

Semegran et al., Lehman Brothers, Inc., Industry Report no. 1565956, pp. 1–77 (page 7, Table 2), 1995.

Ford et al., "Behaviour of insecticide Deposits and Their Transfer from Plant to Insect Surfaces," *Pesticides on Plant Surfaces*, published by John Wiley & Sons for the Society of Chemical Industry, pp. 26–81.

Kirkwood, "Uptake and Movement of Herbicides from Plant Surfaces and the Effects of Formulation and Environment Upon Them," *Pesticides on Plant Surfaces*, published by John Wiley & Sons for the Society of Chemical Industry, pp. 1–25.

Ford, "Insecticide Exposure, Pick–up and Pharmacokinetics with Target and Non–target Insects," *Apsects of Applied Biology*, 31, 1992, pp. 29–41.

Crease et al., "The Use of High Viscosity Carrier Oils to Enhance the insectiicidal Efficacy of ULV Formulations of Cypermethrin," *Aspects of Allied Biology*, 14, 1987, pp. 307–322.

*Primary Examiner*—Jose' G. Dees
*Assistant Examiner*—Alton Pryor
*Attorney, Agent, or Firm*—Banner & Witcoff, Ltd.

[57] ABSTRACT

A pyrethroid insecticide adjuvant composition includes one or more alkyl estes of fatty acids having a level of unsaturation of at least 40% or one or more alkyl esters of dibasic acids and one or more non-ionic emulsifier(s).

30 Claims, 12 Drawing Sheets

Figure 7 — ULV Fastac formulations
Fastac 1l/ha + D100 1l/ha

× Fastac 1l/ha and D100 1l/ha   ▽ Fastac ULV blank no a.i.   ▲ Shell D100 blank no a.i.

Figure 8 — ULV Fastac formulations
Fastac 1l/ha + D100 1l/ha

× Fastac 1l/ha and D100 1l/ha   ▽ Fastac ULV blank no a.i.   ▲ Shell D100 blank no a.i.

Fastac and EOP o:
Concentrate diluted 1:10 with water

% Knockdown vs Log time (minutes)

× Fastac EC 1% w/v a.i.   ▽ Fastac EC 0.001% w/v a.i.   ▲ EOP 1% w/v a.i.
□ EOP 0.001% w/v a.i.    ✶ MOP 1% w/v a.i.               ● MOP 0.001% w/v a.i.

Figure 16

Esterol 123 and 1.12
Modified EC Lambda-cyhalothrin

% Knockdown vs Time (minutes)

× EC no adjuvant    ▽ EC plus 5% Est123    ▲ EC plus 5% Est112
□ EC plus 1% Est123  ✶ EC plus 1% Est112

INSECTICIDE ADJUVANTS

FIELD OF THE INVENTION

This invention relates to compositions that are used as adjuvants to facilitate the effectiveness of insecticides. In particular, these adjuvants have application to pyrethroid insecticides.

BACKGROUND TO THE INVENTION

To maximise crop yields it has become essential to eliminate or substantially reduce the damage that pests inflict on crops. To this end, the chemical industry has developed a range of pesticides to combat most insects.

However, the man on the land daily faces the competing tension between the persistent pests which would reduce his crop yields and the environmental impact which can occur through use of pesticides. Accordingly, there has long been a continuing investigation into the best means to maximise pesticidal efficacy whilst minimising environmental damage.

Current general concerns to reduce pesticide input in farming have raised questions about how this can be achieved quickly, cost effectively and in a manner which is environmentally acceptable. It is now recognised that by integrating formulation and application procedures, increased efficacy of agrochemical treatments is possible thereby reducing the mass of application of active ingredient (a.i.) necessary to control weeds, pests and diseases as disclosed in "The Behaviour of Pyrthroid Insecticide Deposits and their Transfer from Plant to Insect Surfaces," Ford, M. G. and Salt, D. W., in "Pesticides on Plant Surfaces," Critical Reviews in Applied Chemistry, (1987), 18, 26–28, Ed. Cottrell, H. J..

Furthermore, integration of these procedures may lead to selective treatments based on broad spectrum products as disclosed in "Pyrethroid Insecticide Exposure, Pick-up and Pharmacokinetics with Target and Non-target Insects," Ford, M. G., in "Interpretation of Pesticide Affects on Beneficial Anthropods," Aspects of Applied Biology, (1992), 24, 29–41, Ed. Brown, R. A., Jepson, P. C., Sotherton, N. W. Association of Applied Biologists, Wellesbourne.

The use of spray adjuvants is an illustration of how this approach is being applied by farmers who wish to reduce costs and protect the environment by reducing pesticide inputs on their farms. Most research to date concerns spray additives to enhance the performance of herbicides in crop protection. These materials include surfactants and petroleum oils which can be harmful to the environment.

A particular insecticide is Fastac™ (American Cyanamid Company) which has alpha-cypermethrin as its active insecticide ingredient. This product is available in an emulsifiable concentrate (EC) or as an ultra low volume (ULV) formulation for specialist low volume aerial application. The bulking agent is usually a paraffinic oil.

Materials derived from plant oils which are non-toxic, biodegradable and therefore less hazardous are being considered for use as adjuvants in farming operations as disclosed in International Patent Application No. PCT/AU94/00229 by Victorian Chemical Co. Pty. Ltd. and Wilbur-Ellis Company. In that patent application, ethylated esterified seed oils are used to improve the efficacy of herbicide, crop desiccant and defoliant treatments by softening the leaf waxes and enhancing penetration.

SUMMARY OF THE INVENTION

It has now been surprisingly found that certain adjuvants enhance the activity of pyrethroid insecticides. In particular the synthetic pyrethroids have been enhanced. Typical of these pyrethroids are alpha-cypermethrin and lambda-cyhalothin, the latter being the active insecticide ingredient in the emulsifiable concentrate, Karate™ (ICI Australia Limited).

According to the invention, an adjuvant is provided for use with a pyrethroid insecticide including one or more alkyl esters of fatty acids having a level of unsaturation of at least 40%. Higher levels of unsaturation are preferred (eg. at least 50%) being more effective as penetrants. Preferably, the alkyl esters are ethyl or methyl esters. The ethyl esters are most preferred.

DETAILED DESCRIPTION OF THE INVENTION

There are innumerable variations of the preferred ethyl ester since the ethyl esters of fatty acids may be produced from the natural oils and fats such as lard, tallow and vegetable oils or from specific blends produced by fatty acid manufacturers or from fatty acids produced by synthetic means. Readily available commercial vegetable oils such as canola, corn, sunflower and soyabean oils are also sources for fatty acids. Such fatty acids will generally be described in this patent specification as unsaturated fatty acids or oleates.

In another embodiment of the invention, an adjuvant is provided for use with a pyrethroid insecticide including one or more alkyl esters of dibasic acids. A preferred ester is a maleate ester (eg. di-isooctylmaleate).

The adjuvant of the invention may be incorporated with the active insecticide and be applied or diluted prior to application. Alternatively, the adjuvant may be added to a mixture of insecticide and diluent that is otherwise ready for application.

Preferably, the adjuvant is added to an insecticide in an amount of at least 0.5% v/v. Where the application of the insecticide is as a ULV formulation, the adjuvant may exceed 80%, as the adjuvant is also acting as the diluent of the insecticide. However, when the addition of the adjuvant is not for diluent purposes, it is preferably present in amounts of from 0.5 to 25% v/v, more preferably 1 to 10% v/v and most preferably about 2 to 5% v/v.

In this specification when reference is made to the concentration of adjuvant, it means the adjuvant concentration on a v/v basis of the final mixture ready to be applied eg. sprayed.

In another preferred embodiment of the invention, the composition includes a non-ionic emulsifier. These are well known to those skilled in the art and it is recognised that there are a multitude of combinations. Preferably, a non-ionic ester of the fatty acid moiety provides unexpected emulsification and coupling effects to furnish a finished homogeneous product. The non-ionic emulsifier works to provide the preferred emulsification characteristics of the alkyl esters.

In another preferred embodiment, the non-ionic emulsifiers are a combination of alkylaryl ethoxylate and a polyethyleneglycol (PEG) ester of fatty acids. Preferably, the alkylaryl ethoxylate is obtained by reacting any one of the group of alcohols selected from octyl-, nonyl- or dodecylphenol with 3 to 13 moles of ethylene oxide, whilst the PEG ester is of molecular weight range 200–600 with either one or two moles of unsaturated fatty acids.

Whilst it is acknowledged that the emulsifiers outlined above cover a wide range of physical properties and provide wide ranging emulsification abilities, it is important to note that a balance between two quite different emulsifiers can produce a far greater effect than an intermediate emulsifier. With this in mind, many combinations of alkylaryl ethoxylates and PEG esters can provide adequate emulsification of alkyl esters of unsaturated fatty acids for adjuvant systems. A preferred combination is ethoxylated nonylphenol with 9 moles of ethylene oxide and PEG 400 di-oleate in the ratio 1:2 by weight.

In another preferred embodiment, the non-ionic emulsifier is the ethoxylated soy-amine base. A preferred emulsifier would have 15 moles of ethoxylation.

In other preferred embodiments, other non-ionic emulsifiers of interest are those selected from the group of fatty alcohols. A preferred emulsifier would comprise a fatty acid having 6 moles of ethoxylation on the 12 carbon alcohol.

In another preferred embodiment of the invention, a method of treating insects is provided which includes the application to a crop of a pyrethroid insecticide and an adjuvant including one or more alkyl esters of fatty acids having a level of unsaturation of at least 40% or one or more alkyl esters of dibasic acids.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

The invention will now be further illustrated with reference to the following non-limiting examples.

EXAMPLES

Series 1

Materials and Methods

An investigation was carried out to show how the process of dose transfer, penetration and distribution of alpha-cypermethrin are affected by the use of the adjuvants Esterol 123, Vicchem EOP and Vicchem DOP (Victorian Chemical Company, Richmond, Victoria, Australia) and how any changes might modify the effectiveness of alpha-cypermethrin as a contact pyrethroid insecticide.

Esterol 123 is the proprietary product made by Victorian Chemical Company and is substantially ethyl oleate material.

Vicchem EOP is the proprietary product made by Victorian Chemical Company and is a combination of Esterol 123 and non-ionic emulsifiers such that the proportions of constituents (% w/w) are:

| | |
|---|---|
| *Esterol 123*/ethyl oleate | 76 |
| PEG 400 di-oleate | 16 |
| Nonylphenol ethoxylate (9EO) | 8 |

Vicchem DOP is the proprietary product made by Victorian Chemical Company and is a combination of di-isooctylmaleate and non-ionic emulsifiers such that the proportions of constituents (% w/w) are:

| | |
|---|---|
| Di-isooctylmaleate | 76 |
| PEG 400 di-oleate | 16 |
| Nonylphenol ethoxylate (9EO) | 8 |

Alpha-cypermethrin is a commercially available emulsifiable concentrate Fastac™ EC, 100 g a.i./l.

Penetration studies using isolated insect cuticles

Penetration of topically applied alpha-cypermethrin (4 $\mu$l of an aqueous solution of Fastac™ EC containing 1% a.i. w/v) across isolated cuticles of final instar larvae of *Spodoptera littoralis* Boisd. was studied using a diffusion flow cell. Changes in the solute concentrations in the receptor solvent were monitored at 220 nm wavelength at 10 second intervals. The penetrations rates for Fastac™ EC (1% w/v of a.i. as above) with and without Esterol 123, Vicchem EOP or Vicchem DOP (1% v/v) were compared to establish whether these adjuvants modify cuticle permeability.

Droplet ageing on glass slides

Esterol 123, Vicchem EOP and Vicchem DOP were added to the Fastac™ EC already diluted to 1% a.i. w/v with distilled water to give final solutions containing 1, 5, 10 or 25% v/v of adjuvant. Droplets (20 $\mu$l) of each solution were applied to glass microscope slides and left to dry. For comparison, droplets of pure Vicchem EOP and Vicchem DOP were also prepared. The effect of deposit ageing was assessed throughout a 24 hour period.

Pick-up, penetration and redeposition of alpha-cypermethrin

Pick-up of alpha-cypermethrin from droplets placed on glass slides was investigated to determine whether addition of adjuvant enhanced dose transfer. Adult mustard beetles held dorsally by a suction footer were placed in contact with the centre of a deposit for 2 seconds, removed to a petri dish and left for 2 hours before being immersed in Analar acetone to remove transferred pyrethroid insecticide. The beetles were removed and the washings analysed for alpha-cypermethrin using electron capture detection (ECD) on a Hewlett Packard 1580 gas chromatograph (GC). The washed beetles were then frozen in liquid nitrogen to remove tissue water, crushed and further extracted in acetone to determine the internal concentrations of penetrated alpha-cypermethrin using ECD GC.

Beetles were held as before in order to contact deposits containing the diluted EC (1% w/v alpha-cypermethrin) and known amounts of adjuvant (Vicchem EOP or Vicchem DOP). Redeposition of alpha-cypermethrin onto glass surfaces was followed for five successive contacts (2 sec per contact) in order to estimate the retained fraction. The contaminated beetles and glass surfaces were washed immediately with acetone and analysed for alpha-cypermethrin using a Hewlett Packard GCD (ion-selective mode).

Response to mustard beetles following contact with aged deposits

Beetles were held for 2 seconds in contact with deposits prepared earlier from solutions containing known amounts of alpha-cypermethrin and adjuvant. The treated insects were then confined to filter paper lined petri dishes. Knockdown and mortality were observed at frequent intervals after treatment.

Results

Penetration studies using isolated insect cuticles

Figure 1:
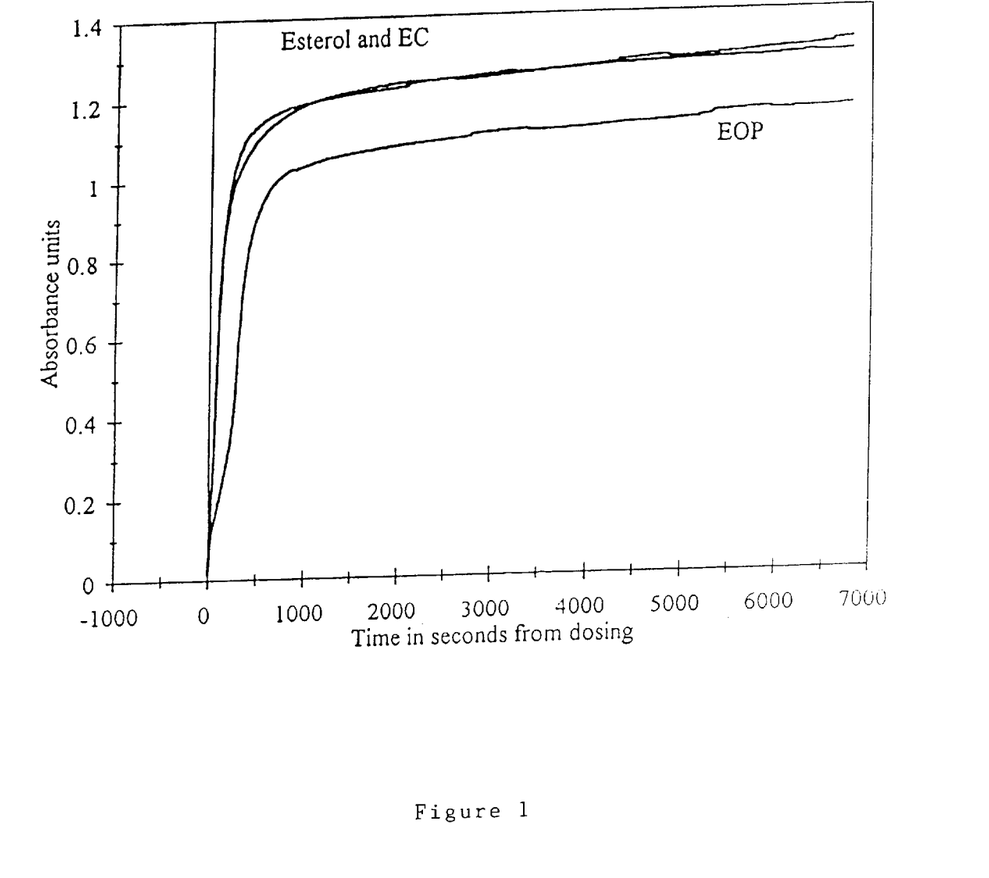
FIG. 1 depicts penetration profiles for EC formulations containing 1% w/v alpha-cypermethrin with and without Esterol 123, Vicchem EOP, and Vicchem DCP.

Penetration profiles for EC formulations containing 1% w/v alpha-cypermethrin with and without Esterol 123, Vicchem EOP and Vicchem DOP (1% v/v) are presented in Series 1, FIG. 1. All four formulations penetrated the cuticle at matching rates to produce similar absorbency profiles with time. These profiles measure the penetration of all of the formulation components including the active ingredient.

The results suggest that these adjuvants make little difference to the overall permeability of the cuticle as a result of surface effects, for example by modifying the organisation of the epicuticular waxes as suggested for plant cuticles.

Droplet ageing on glass slides

On drying, the EC formulation formed a liquid deposit from which the pyrethroid insecticide crystallised slowly with time. Addition of Esterol 123, Vicchem EOP and Vicchem DOP slowed the ageing process and prevented crystallisation so that deposits remained liquid 24 hours after application to glass. In this fluid state, pyrethroid insecticide deposits are known to be more available for transfer to contacting insects.

Pick-up, redeposition and subsequent penetration of alpha-cypermethrin

Addition of the adjuvants Esterol 123 and Vicchem EOP increased the amount of alpha-cypermethrin initially transferred following a single 2 second contact with deposits aged for four hours after application of 20 μl droplets to glass slides (Table 1). Esterol 123 was the most effective treatment when the adjuvants were added at a concentration of 1% v/v; increasing the adjuvant concentration to 5% v/v increased the transfer of alpha-cypermethrin from the Vicchem EOP and Vicchem DOP formulations to the level attained by Esterol 123 at 1% v/v.

TABLE 1

Recoveries (μg/insect) of alpha-cypermethrin from the transfer to adult mustard beetles following a single 2 second contact between the deposit and the tarsi.

| Adjuvant concentration (% v/v) | 0 | 1 | 5 |
|---|---|---|---|
| Esterol 123 | 0.26 | 14.4 | 15.8 |
| Vicchem BOP | 0.26 | 6.1 | 14.5 |

Redeposition of alpha-cypermethrin following initial contact with deposits prepared from a solution of alpha-cypermethrin and Vicchem EOP (1% w/v) was investigated in a similar manner. Adult beetles were held in contact with deposits for 2 seconds, as before, and then brought into contact with 5 successive clean glass surfaces for the same time to allow any redeposition from the tarsi onto the glass to take place. The contaminated surfaces were washed with acetone and the washings analysed by GCD. Although initial contact with such deposits resulted in an average transfer of 3 μg/insect, no subsequent redeposition was detected. Thus, the initial amount transferred remained on the insect where it was available for poisoning.

TABLE 2

Recoveries (μg/insect) of alpha-cypermethrin from the surface and internal tissues of adults of *Phaedon cochleariae* Fab. following contact (2 sec) with deposits containing ethylated esterified seed oils.

| Adjuvant concentration (% v/v) | 0 | 1 | 5 | 10 | 25 |
|---|---|---|---|---|---|
| External | | | | | |
| Esterol 123 | 0.94 | 1.92 | 3.30 | 2.84 | 2.06 |
| Vicchem EOP | 0.94 | 1.96 | 3.52 | 2.08 | 3.62 |
| Internal | | | | | |
| Esterol 123 | 0.33 | 1.02 | 2.58 | 1.20 | 1.32 |
| Vicchem EOP | 0.33 | 0.33 | 5.90 | 3.72 | 1.59 |

Penetration of acquired alpha-cypermethrin was investigated following 2 second contacts of beetles with deposits formed from formulations containing different amounts of adjuvant. Analysis of the quantities recovered from the beetle surface and the internal extracts (Table 2) suggests an optimum adjuvant concentration (5% v/v) which gave maximal dose transfer and internal accumulation of alpha-cypermethrin 4 hours after contact. Thus, the adjuvant is seen to have some effect on cuticular penetration and the concentration sprayed is also significant.

Figure 2:
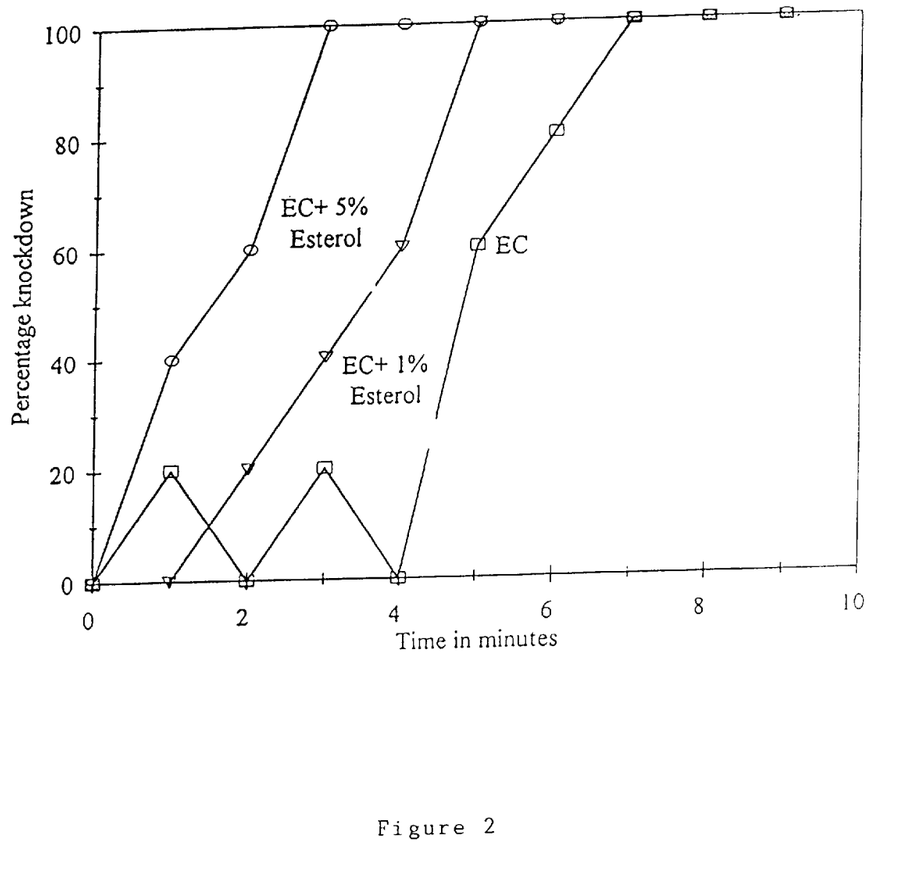
FIG. 2 depicts the influence of ethylated esterified seed oils on insect response.
Figure 3:
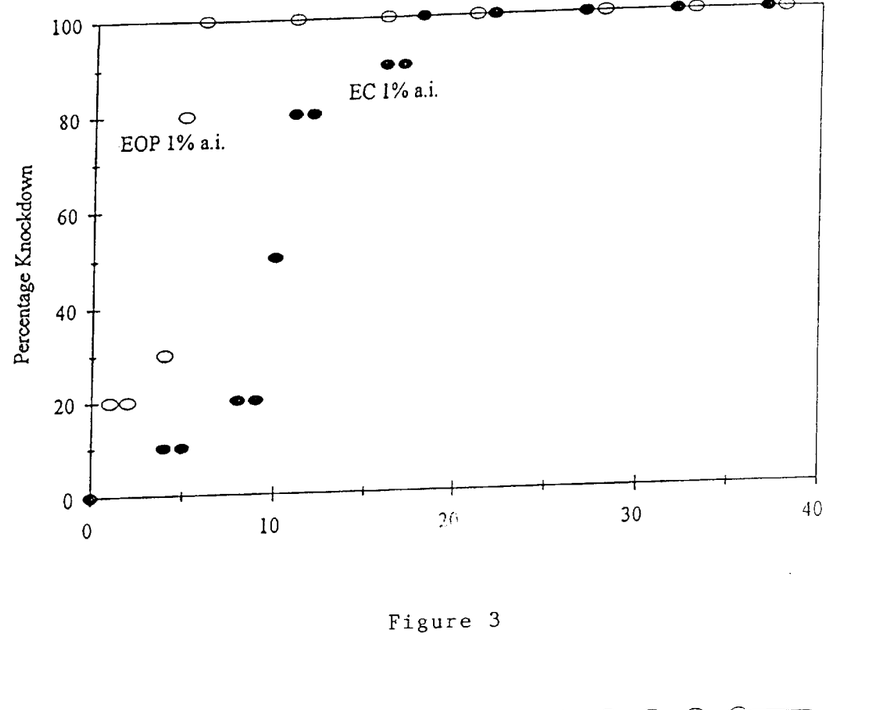
FIG. 3 depicts the influence of ethylated esterified seed oils on insect response.
Figure 4:
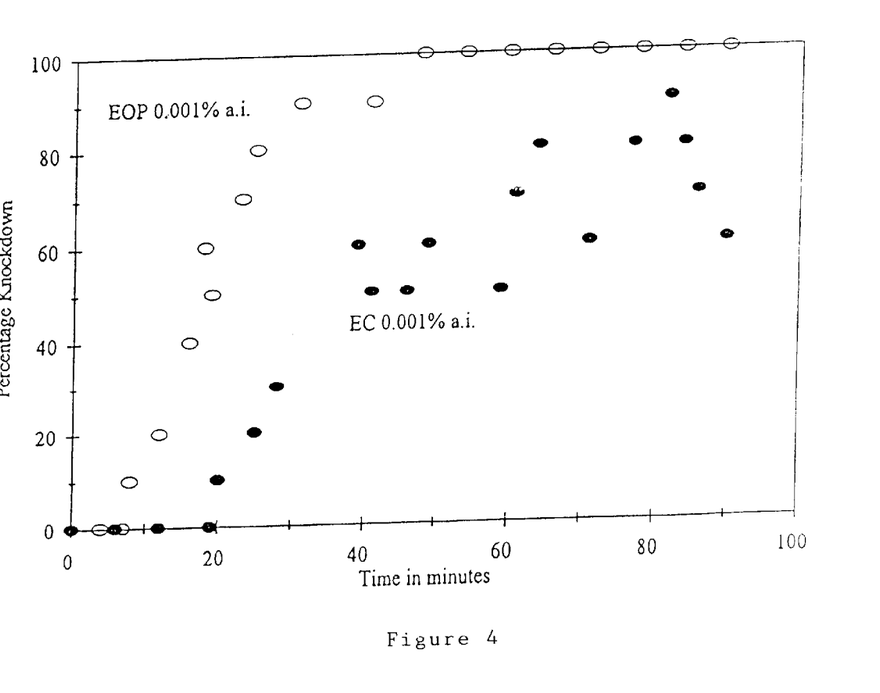
FIG. 4 depicts the influence of ethylated esterified seed oils on insect response.

Response of mustard beetles following contact with deposits of alpha-cypermethrin The influence of ethylated esterified seed oils on the insect response was investigated and is depicted in Series 1, FIGS. 2, 3 and 4.

At the recommended field rate of 1% w/v alpha-cypermethrin, a Fastac™ EC formulation containing adjuvants such as Esterol 123 produce quicker knockdown in adult mustard beetles, *Phaedon cochleariae* Fab., than the same formulation applied alone. Similar results were obtained when the adjuvant Vicchem EOP was used as a carrier solvent. Thus, Vicchem EOP has potential as an pyrethroid insecticide carrier (FIGS. 3 and 4). This use of Vicchem EOP, for example, gave 100% knockdown at a concentration of alpha-cypermethrin of 0.001% a.i. w/v. The same concentration of a.i. resulted in only 60–80% knockdown (the upper response limit) following contact with deposits containing Fastac™ EC, suggesting that use of the adjuvant as a carrier increases insecticidal efficacy (FIG. 4). Thus, effective treatments are possible using less pyrethroid insecticide.

This study suggests that the use of adjuvants derived from ethylated esterified seed oils increases the efficacy of the contact pyrethroid insecticide alpha-cypermethrin in a dose-related manner. The effect results primarily from an increased transfer of pyrethroid insecticide to adult mustard beetles. *Phaedon cochleariae* Fab. following contact with residual deposits. The higher internal levels of toxin which are observed 4 hours after encountering a deposit and associated changes in the speed of intoxication probably reflect this enhanced pick-up, although changes in the rate of cuticular penetration cannot be entirely discounted. Use of Vicchem EOP as a carrier solvent for alpha-cypermethrin resulted in a more effective treatment than Fastac™ EC applied at an equivalent concentration (0.001% a.i. w/v). It should therefore be possible to reduce the quantity of pyrethroid insecticide sprayed either by adding an appropriate adjuvant to the tank mix or by reformulating alpha-cypermethrin in a novel carrier such as Vicchem EOP.

EXAMPLES

Series 2

Materials and Methods

These studies were undertaken to investigate the efficacy of Esterol 112 (also obtained from Victoria Chemical Company) and Esterol 123 as bulking oils.

Esterol 112 is the proprietary product made by Victorian Chemical Company and is substantially methyl oleate material.

Vicchem MOP is the proprietary product made by Victorian Chemical Company and is a combination of Esterol 112 and non-ionic emulsifiers such that the proportions of constituents are:

| | |
|---|---|
| *Esterol 112*/methyl oleate | 76 |
| PEG 400 di-oleate | 16 |
| Nonylphenol ethoxylate (9EO) | 8 |

Esterol 123, Vicchem EOP and Vicchem DOP are as described in the Series 1 examples.

Fastac™ ultra low volume (ULV) containing 1% w/v alpha-cypermethrin, (obtained from Cyanamid, Gosport, UK) was used as the commercial pyrethroid insecticide. This ULV formulation was mixed with the following oil adjuvants (co-diluents):

Shellsol D100 (a petroleum derived solvent which has been highly defined to convert aromatics to cycloparaffins (Shell International));

Esterol 123 and Esterol 112.

Penetration studies using isolated insect cuticles, the pick-up, penetration and redeposition of alpha-cypermethrin and the response of mustard beetles following contact with aged deposits were as described in the Series 1 examples.

Results

Response of Fastac™ ULV blank and each adjuvant alone

Figure 5:
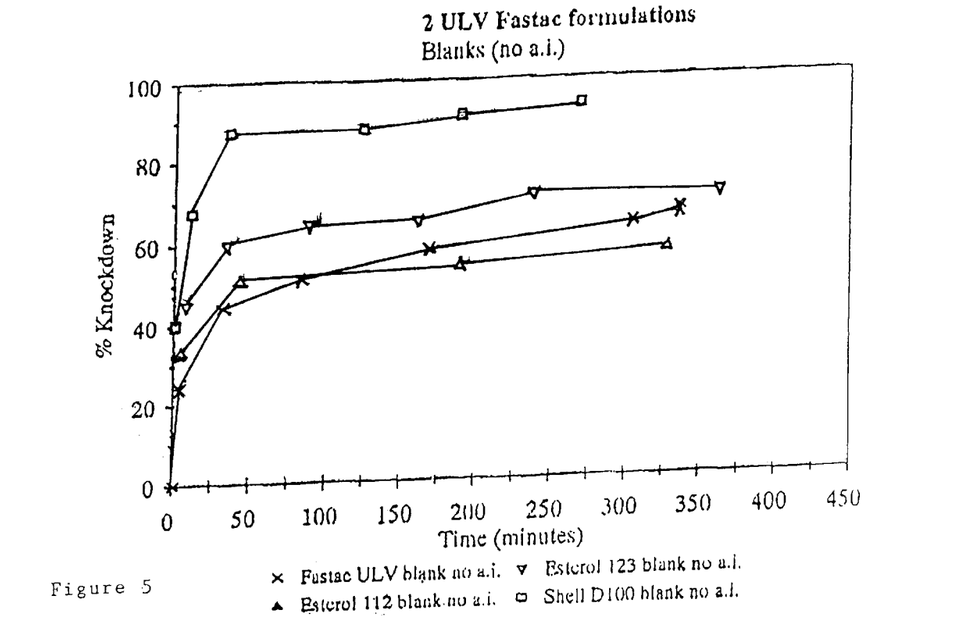
FIG. 5 depicts knockdown results of various undiluted oils.
Figure 6:
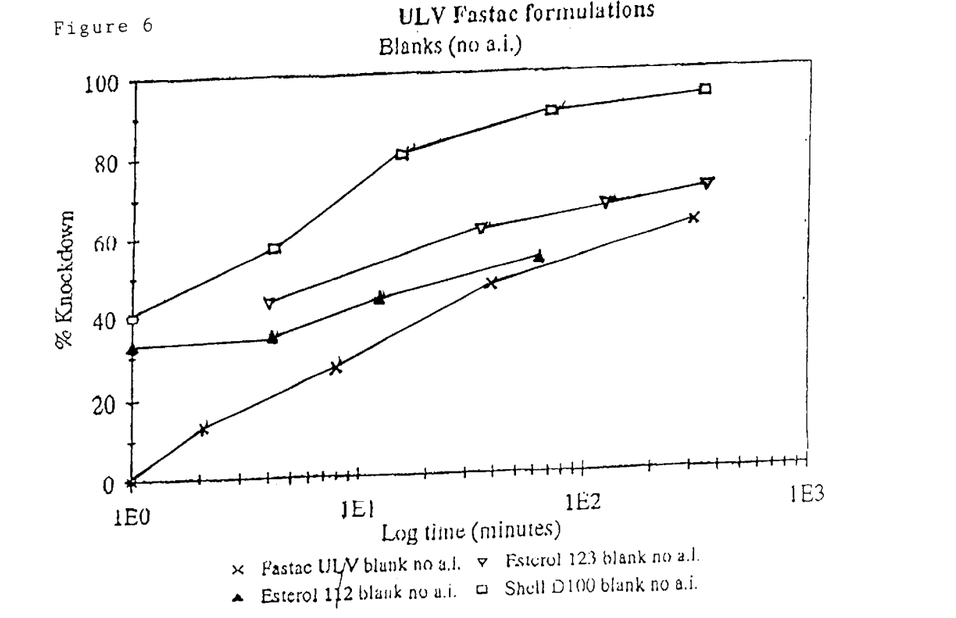
FIG. 6 depicts knockdown results of various undiluted oils.

The results from Series 2, FIGS. 5 and 6, show that each oil induces knockdown in adult mustard beetles brought into contact with a 4 hour old deposit placed on a glass slide. Complete recovery was observed twelve hours after contact with the Fastac™ ULV blank. However, there was no significant recovery after contact with Esterol 123, Esterol 112 or Shellsol D100. These results demonstrate that undiluted oils can themselves exert some insecticidal activity.

Figure 7:
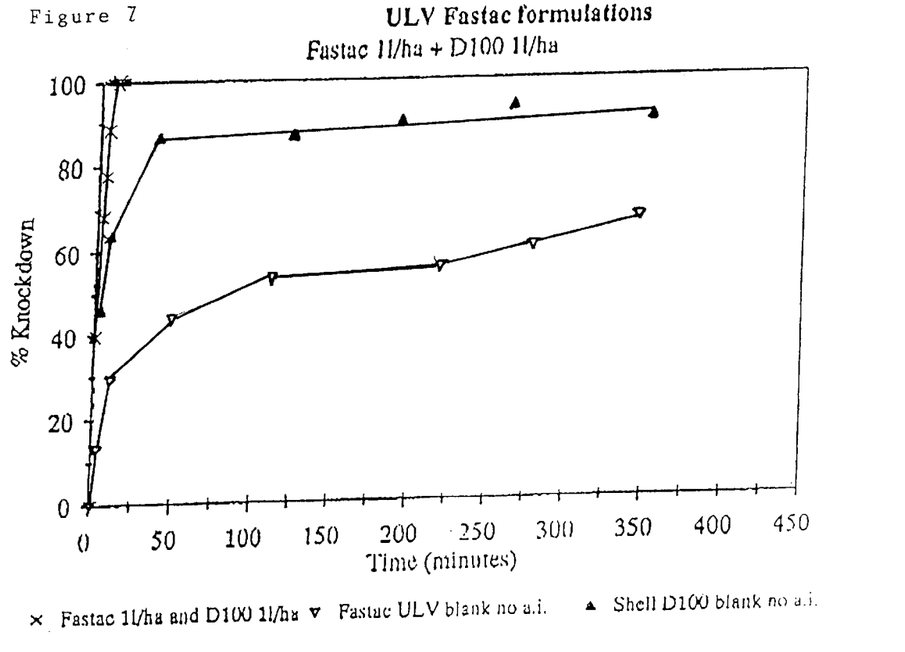
FIG. 7 depicts knockdown results of mixture of oils.
Figure 8:
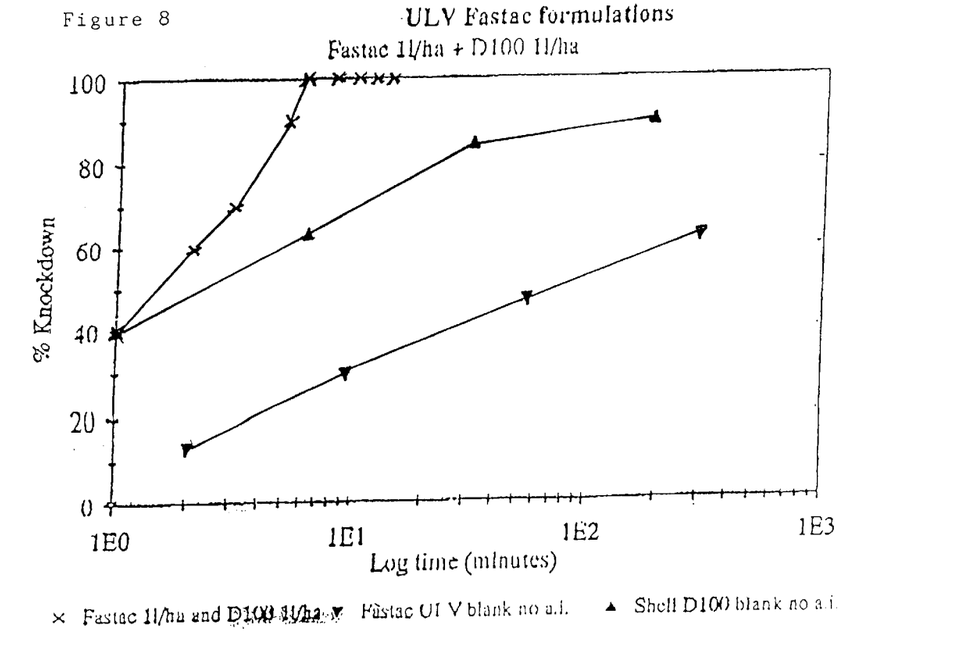
FIG. 8 depicts knockdown results of mixture of oils.

In Series 2, FIGS. 7 and 8 show that a mixture containing 50% by volume 1% a.i. w/v Fastac™ ULV and 50% by volume Shellsol D100 gave 100% knockdown and was faster acting than either the Fastac™ ULV blank or the Shellsol D100 bulking oil. Neither of the alpha-cypermethrin blanks gave complete knockdown.

Figure 9:
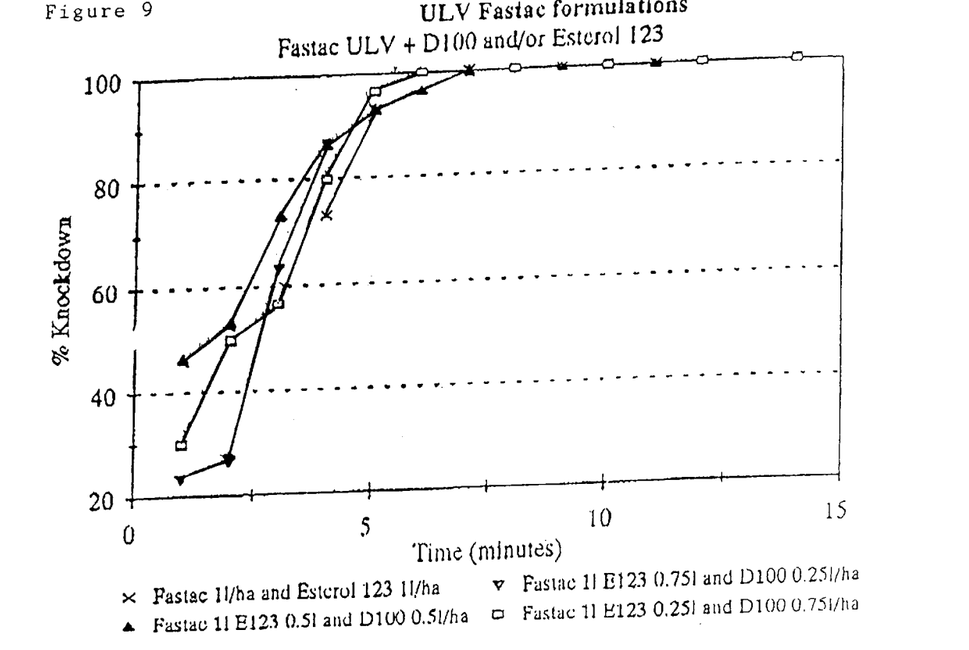
FIG. 9 depicts knockdown results of different ratios of oils.
Figure 10:
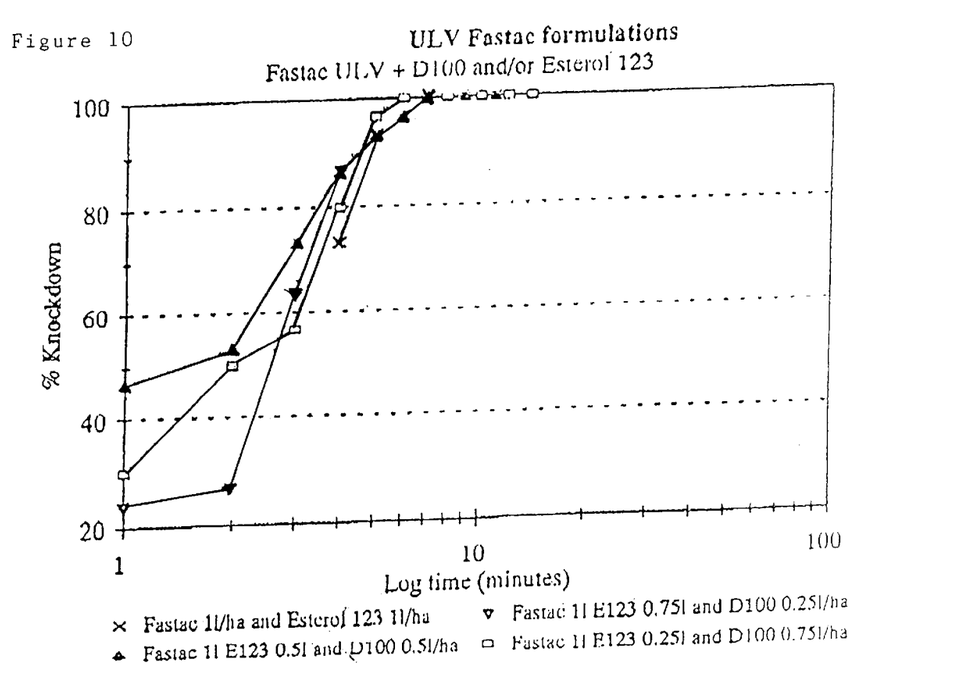
FIG. 10 depicts knockdown results of different ratios of oils.

When Esterol 123 was mixed in different proportions with commercial bulking oil, Shellsol D100, for use as for the ULV formulation Fastac™ (1T a.i.), changing the ratio of adjuvants but maintaining the Fastac™ at 50% v/v had no effect on the speed of knockdown as illustrated in Series 2, FIGS. 9 and 10. This result shows that Esterol 123 and Shellsol D100 are equally effective as bulking oils for this formulation of alpha-cypermethrin.

However, all four mixtures of adjuvants gave 100% mortality after 12 hours, whereas that containing only Shellsol D100 gave approximately 17% recovery of the mustard beetles. This result indicates that greater dose transfer of alpha-cypermethrin is obtained in the presence of the adjuvants.

Figure 11:
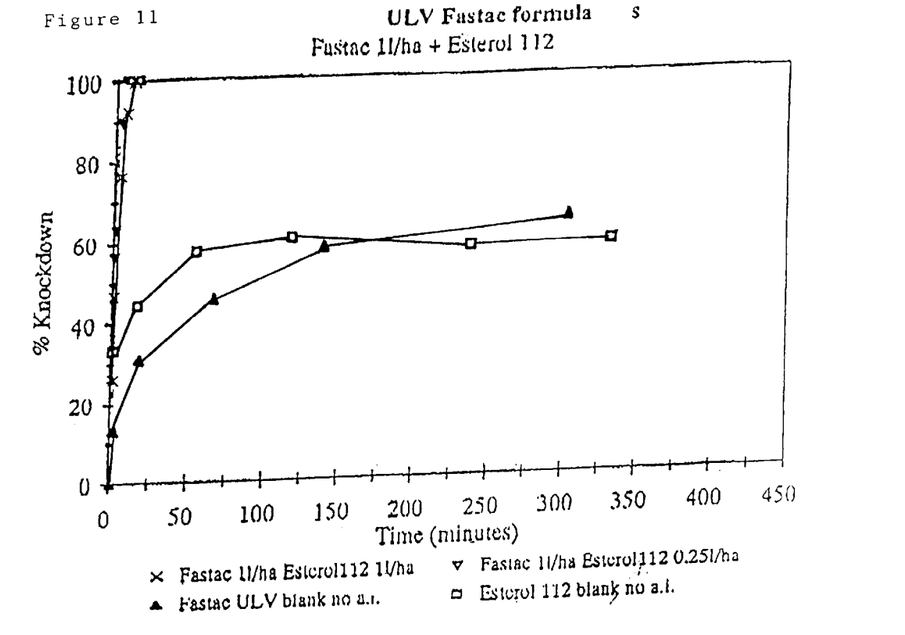
FIG. 11 depicts knockdown results of different concentrations of Fastac™.
Figure 12:
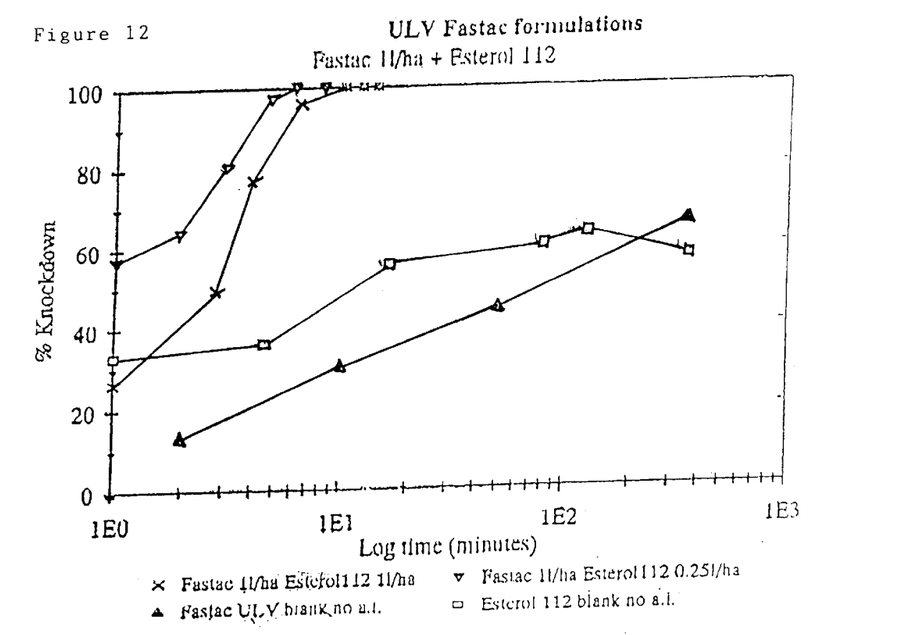
FIG. 12 depicts knockdown results of different concentrations of Fastac™.

In another experiment, Fastac™ ULV 1% w/v was diluted by 50% and 20% v/v, respectively with Esterol 112 to give mixtures containing different concentrations of Fastac™ formulation components including alpha-cypermethrin. The results from Series 2, FIGS. 11 and 12, confirm that mixtures containing a.i. are much faster acting than the blanks. Furthermore, the formulation containing the smallest amounts of Esterol 112, and therefore the greatest concentration of alpha-cypermethrin appears to be the fastest acting mixture. Only the mixtures containing a.i. gave 100% mortality.

Figure 13:
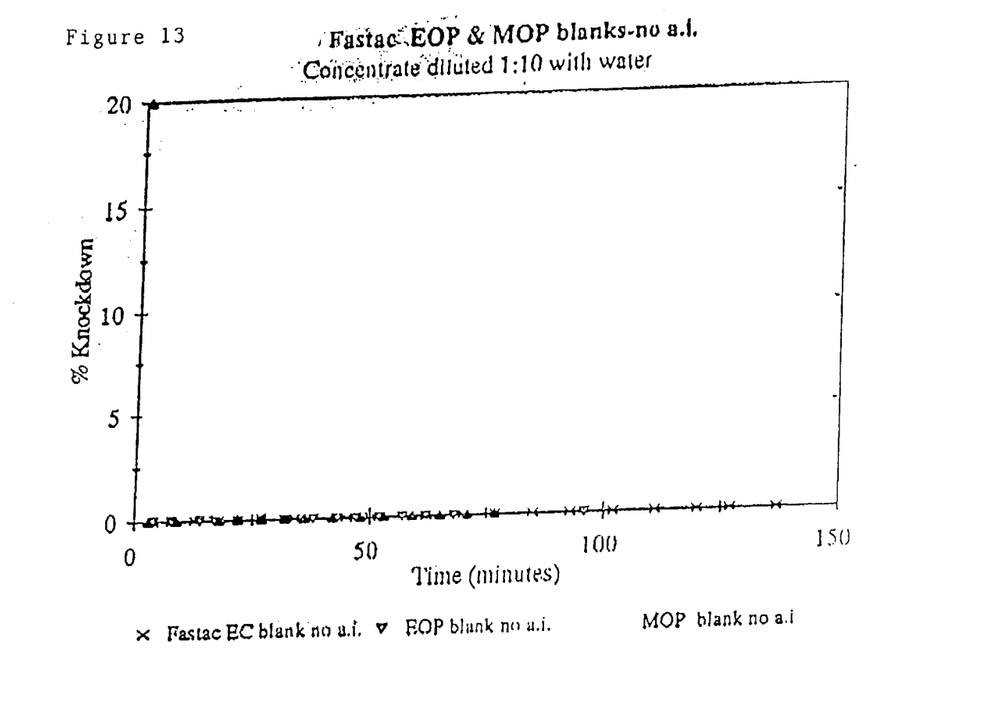
FIG. 13 depicts the benefits of addition of adjuvants.
Figure 14:
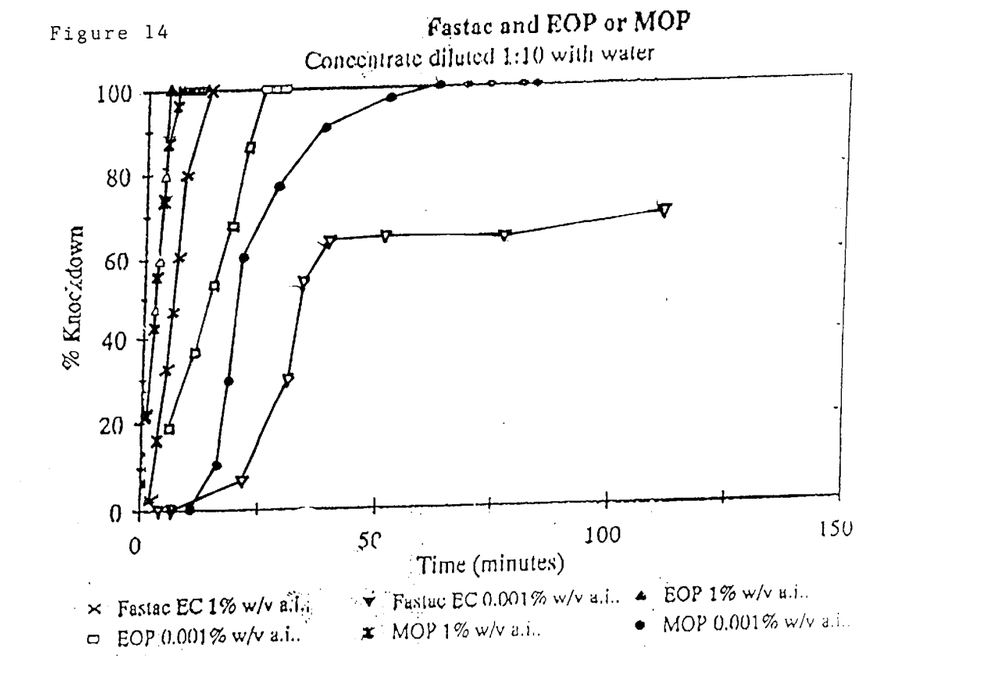
FIG. 14 depicts the benefits of addition of adjuvants.
Figure 15:
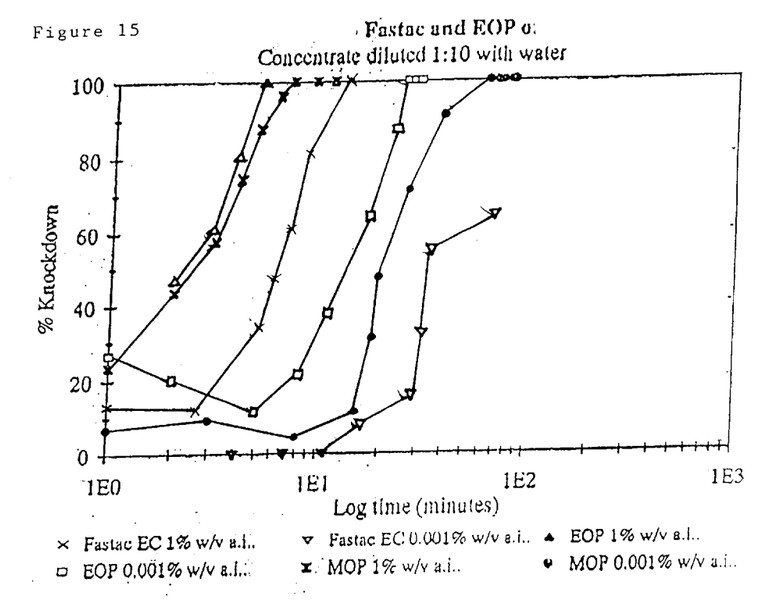
FIG. 15 depicts the benefits of addition of adjuvants.

The responses due to alpha-cypermethrin dissolved in Vicchem EOP, Vicchem MOP or Fastac™ EC blank prior to final dilution with water to give concentrations of a.i. of 0.001% and 1% w/v were also compared directly. The results show that at both concentrations of alpha-cypermethrin, the addition of adjuvants produced faster knockdown. The results at 0.001% w/v a.i. demonstrate the benefits of addition of adjuvants most clearly in Series 2, FIGS. 13, 14 and 15.

The formulation containing alpha-cypermethrin dissolved in Vicchem EOP gave the most rapid knockdown, followed by that dissolved in Vicchem MOP; the Fastac™ blank gave the slowest knockdown. This ranking was also observed at the higher concentration of a.i. (1% w/v). Percentage mortality follows the same trend. At 0.001% a.i., Fastac™ EC alone gave only 47% kill 24 hours after contact. Addition of Vicchem EOP and Vicchem MOP always resulted in 100% kill with 0.001% a.i. alpha-cypermethrin.

EXAMPLES

Series 3

The materials and methods, the pick-up, penetration and redeposition of lambda-cyhalothrin and the response of mustard beetles following contact with aged deposits were as described in the Series 1 examples.

Results

Figure 16:
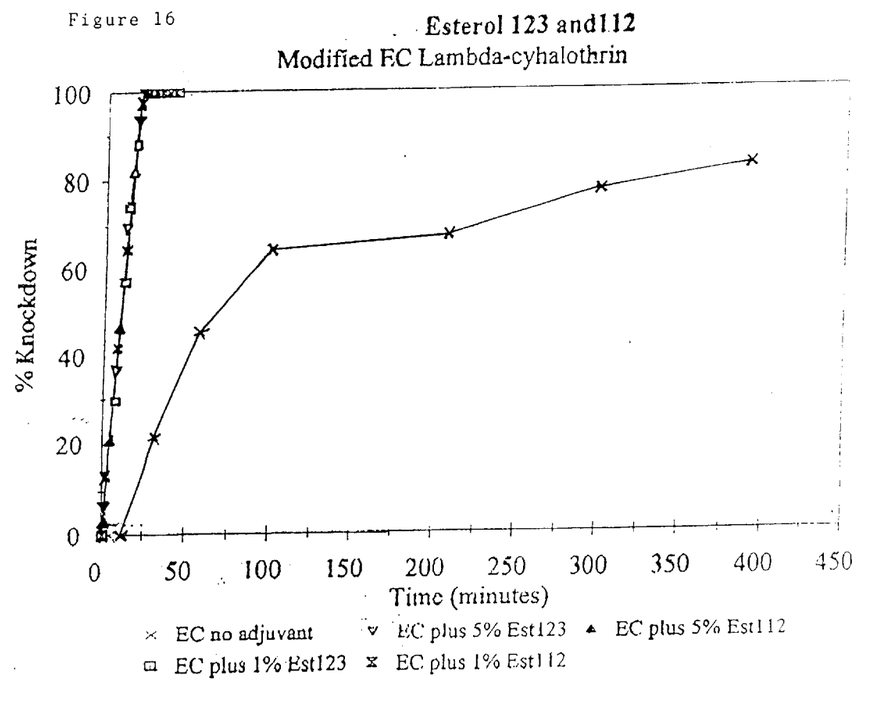
FIG. 16 is a comparison of insecticides and adjuvant mixtures compared with pyrethroid lambda-cyhalothrin alone.

Each of the insecticides and adjuvant mixtures was very effective compared with the pyrethroid lambda-cyhalothrin alone as shown in Series 3, FIG. 16. The insecticide with Esterol 112 and Esterol 123 at 5% v/v were the most effective initially exhibiting a higher knock down rate than insecticide compositions having 1% of these adjuvants. However, all the adjuvant and insecticide mixtures showed superior knock down rates to the insecticide not mixed with the adjuvants. This shows that these adjuvants improve the insecticidal performance of lambda-cyhalothrin.

EXAMPLES

Series 4

Materials and Methods

A series of laboratory bioassays was carried out to determine if Vicchem EOP could improve the efficacy of the synthetic pyrethroids Bulldock EC (Bayer; betacyfluthrin at 25 g a.i./liter) and Decis Forte EC (AgrEvo; deltamethrin at 27.5 g a.i./liter). Black field crickets were treated with 2.0% composition of Vicchem EOP.

The black field cricket (*Teleogryllus commodus*) is a chewing insect and the first instars (i.e. newly emerged crickets) from a laboratory culture were used to test these pyrethroids. The culture was maintained at 24° C. in a controlled-temperature room. The adults were reared from nymphs in ventilated plastic containers. The crickets were fed grain pellets throughout their life stages. Equal numbers of males and females were present and first instars were removed daily for bioassays.

Insecticides in all treatments were applied using a Potter tower (Burkard) to ensure consistent application rates. The tower was run at 40 kPa and delivered droplets at about 50 μm in diameter. Plain cabbage was used for the bioassays.

Cabbage leaves were sectioned and placed onto the base of a petri dish (9 cm diam). One side only was sprayed and the leaf section was air-dried for 20 min. in a fume-hood. Controls were sprayed with water only. Five sections (replicates) were prepared for each dose. A sharpened steel cutter (18 mm in diam) was used to cut 3 discs from each sprayed section and these were placed into the base of the glass petri dish (9 cm in diam.). First instars were placed into each disc using a camel hair brush, before replacing the lid. Each replicate contained 10 crickets. The bioassays were conducted at 25° C. and cricket mortality was assessed after 24 hours.

An initial comparison was made between sprayed leaf discs and the contact toxicity of the adjuvant and Bulldock EC, sprayed onto the glass only. The adjuvant and Bulldock EC were applied separately at varying rates in order to determine a dose response curve. Petri dish bases (9 cm diam.) were sprayed and then air-dried for 20 min. Controls were sprayed with water only. Five replicates were prepared and each plate was innoculated with 10 crickets. The bioassays were conducted at 25° C. and cricket mortality was assessed after 24 hours.

Results

Figure 17:
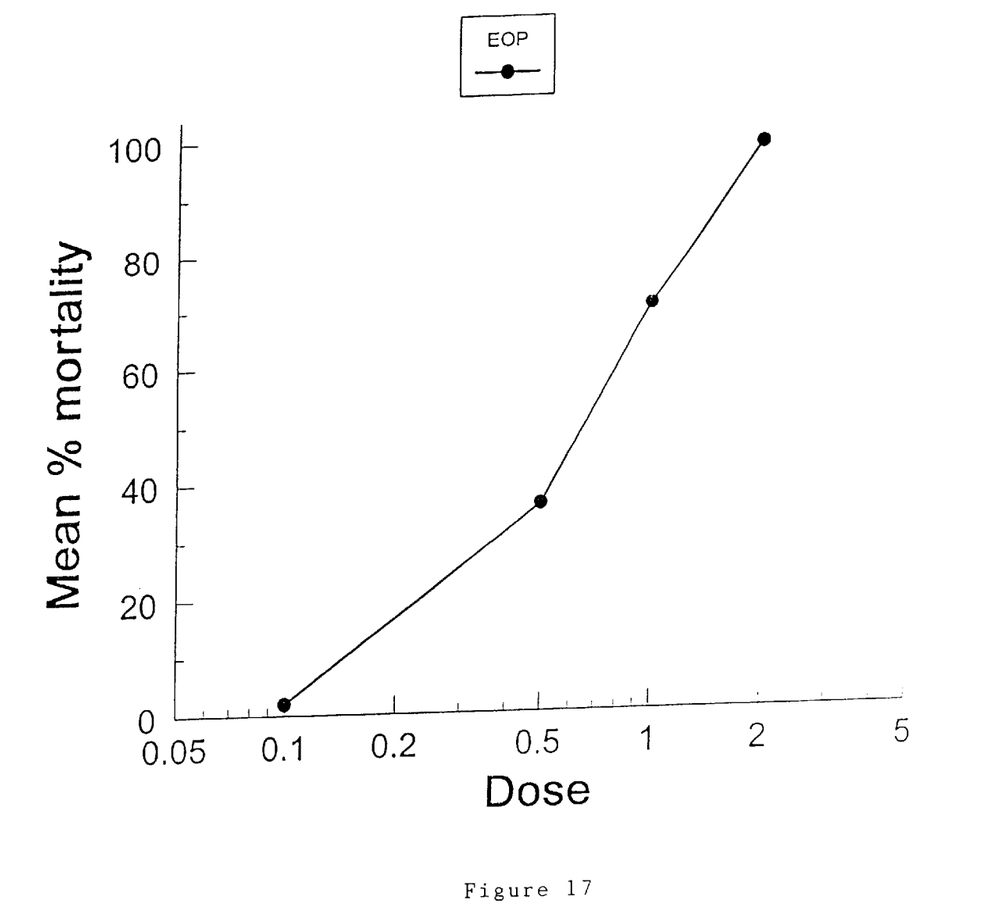
FIG. 17 depicts insecticidal activity of crickets with increasing concentrations of Vicchem EOP.

Vicchem EOP shows insecticidal activity when crickets were placed onto bare treated glass as shown in Series 4, FIG. 17 and mortality increased with the increasing concentrations of Vicchem EOP.

No cricket mortality was recorded with the leaf discs were sprayed with either 0.5% or 2.0% Vicchem EOP. It would appear that this result is due to lower effective doses being available on the leaf discs than on bare glass, or because of penetration of the Vicchem EOP into the leaf tissue, or a combination of both factors.

Figure 18:
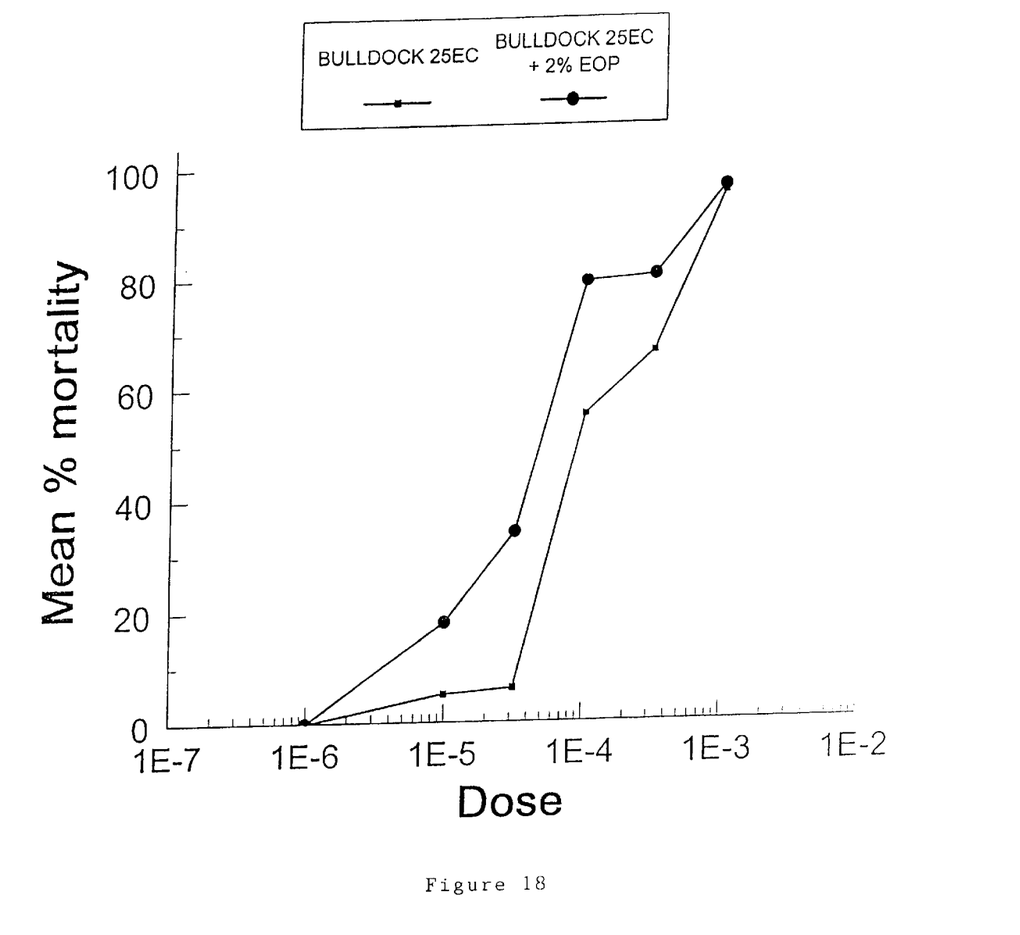
FIG. 18 shows the dose-response curve for synthetic pyrothroids with Vicchem EOP at 2.0% concentration.
Figure 19:
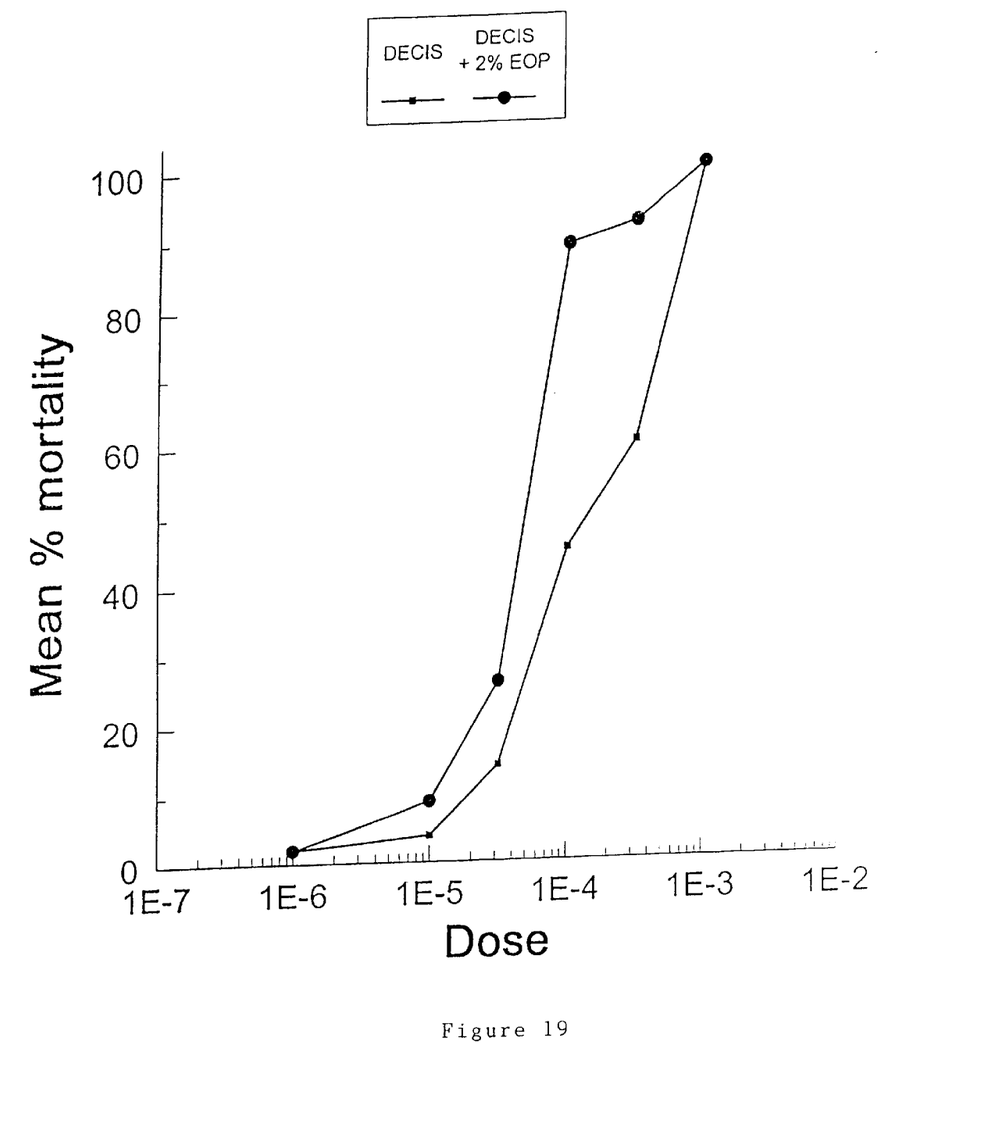
FIG. 19 shows the dose-response curve for synthetic pyrothroids with Decis Forte EC at 2.0% concentration.

Vicchem EOP at a concentration of 2.0% shifted the dose-response curve for the synthetic pyrethroids, Bulldock EC as illustrated in Series 4, FIG. 18 and for Decis Forte EC shown in Series 4, FIG. 19 revealing a significant increase in the relative efficacy of these pyrethroids.

Summary of Results

From the above results as shown in Series 1, 2, 3 and 4 examples, it is apparent that this invention allows the use of enhancing adjuvants for pyrethriod insecticides to either improve their effectiveness or minimise the amount of active ingredient which needs to be applied to crops to kill insects.

We claim:

1. An insecticidal composition comprising a pyrethroid insecticide and an adjuvant composition, said adjuvant composition provided in an amount sufficient to enhance the insecticidal action of said pyrethroid insecticide, said adjuvant composition consisting essentially of (1) an adjuvant, said adjuvant being selected from (i) one or more alkyl esters of fatty acids having a level of unsaturation of at least 40%, or (ii) one or more alkyl esters of dibasic acids, and (2) a non-ionic emulsifier.

2. The insecticidal composition of claim 1 wherein at least 50% of the adjuvant composition is said alkyl esters.

3. The insecticidal composition of claim 2 wherein said adjuvant is an alkyl ester of a fatty acid and has a level of unsaturation of at least 50%.

4. The insecticidal composition of claim 1 wherein said alkyl ester of a fatty acid is a methyl or ethyl ester.

5. The insecticidal composition of claim 4 wherein said alkyl ester is an ethyl ester.

6. The insecticidal composition of claim 2 wherein said adjuvant is an alkyl ester of a dibasic acid.

7. The insecticidal composition of claim 6 wherein said alkyl ester of a dibasic acid is a maleate ester.

8. The insecticidal composition of claim 7 wherein said maleate ester is di-isooctylmaleate.

9. The insecticidal composition of claim 1 wherein the non-ionic emulsifier is a non-ionic ester of a fatty acid.

10. The insecticidal composition of claim 1 wherein the non-ionic emulsifier comprises a combination of two or more non-ionic emulsifiers.

11. The insecticidal composition of claim 1 wherein the non-ionic emulsifier comprises a polyethyleneglycol (PEG) ester of a fatty acid.

12. The insecticidal composition of claim 10 wherein the non-ionic emulsifier comprises a combination of an alkylaryl ethoxylate and a polyethyleneglycol (PEG) ester of a fatty acid.

13. The insecticidal composition of claim 12 wherein the alkylaryl ethoxylate is obtained by reacting an alcohol, selected from the group consisting or octylphenol, nonylphenol, dodecylphenol, and mixtures thereof, with 3 to 13 moles of ethylene oxide.

14. The insecticidal composition of claim 13 wherein the alkylaryl ethoxylate is obtained by reacting nonylphenol with 9 moles of ethylene oxide.

15. The insecticidal composition of claim 14 wherein the polyethyleneglycol (PEG) ester is PEG 400 di-oleate.

16. The insecticidal composition of claim 1 wherein the non-ionic emulsifier comprises a combination of an alkylaryl ethoxylate obtained by reacting nonylphenol with 9 moles of ethylene oxide and PEG 400 di-oleate in a ratio 1:2 by weight.

17. The insecticidal composition of claim 1 wherein the non-ionic emulsifier comprises an ethoxylated soy-amine base.

18. The insecticidal composition of claim 17 wherein the ethoxylated soy-amine base has 15 moles of ethoxylation.

19. The insecticidal composition of claim 1 wherein the non-ionic emulsifier comprises a fatty alcohol.

20. The insecticidal composition of claim 19 wherein the fatty alcohol is a 12 carbon alcohol with 6 moles of ethoxylation.

21. The insecticidal composition of claim 1 wherein the adjuvant comprises at least 0.5% v/v of said insecticidal composition.

22. The insecticidal composition of claim 1 wherein the adjuvant comprises at least 80% v/v of said insecticidal composition.

23. The insecticidal composition of claim 1 wherein the adjuvant comprises from 1.0 to 10% v/v of said insecticidal composition.

24. A method for controlling insect infestation of crops comprising applying to said crops an insecticidally effective amount of an insecticidal composition comprising a pyrethroid insecticide and an adjuvant composition, said adjuvant composition provided in an amount sufficient to enhance the insecticidal action of said pyrethroid insecticide, said adjuvant composition consisting essentially of (1) an adjuvant, said adjuvant being selected from (i) one or more alkyl esters of fatty acids having a level of unsaturation of at least 40%, or (ii) one ore more alkyl esters of dibasic acids, and (2) a non-ionic emulsifier.

25. The method of claim 24 wherein said adjuvant is an methyl or ethyl ester of a fatty acid.

26. The method of claim 24 wherein said adjuvant is an alkyl ester of a dibasic acid.

27. The method of claim 25 wherein said adjuvant is an ethyl ester of a fatty acid.

28. The method of claim 26 wherein said adjuvant is a maleate ester.

29. The method of claim 24 wherein said wherein the non-ionic emulsifier a comprises a combination of an alkylaryl ethoxylate and a polyethyleneglycol (PEG) ester of a fatty acid.

30. The method of claim 29 wherein the non-ionic emulsifier comprises a combination of an alkylaryl ethoxylate obtained by reacting nonylphenol with 9 moles of ethylene oxide and PEG 400 di-oleate in a ratio 1:2 by weight.

* * * * *